United States Patent [19]
Ferguson

[11] Patent Number: 6,093,388
[45] Date of Patent: Jul. 25, 2000

[54] MANNOSE-6-PHOSPHATE COMPOSITION AND ITS USE IN TREATING FIBROTIC DISORDERS

[75] Inventor: Mark William James Ferguson, Stockport, United Kingdom

[73] Assignee: BTG International Limited

[21] Appl. No.: 09/243,531

[22] Filed: Feb. 3, 1999

Related U.S. Application Data

[63] Continuation of application No. PCT/GB97/02076, Jul. 31, 1997.

[30] Foreign Application Priority Data

Aug. 12, 1996 [GB] United Kingdom .................... 9616896

[51] Int. Cl.$^7$ ............................ A61K 31/74; A61F 13/00
[52] U.S. Cl. ........................................ 424/78.04; 424/443
[58] Field of Search .................................. 424/78.04, 443

[56] References Cited

U.S. PATENT DOCUMENTS 5,244,651  9/1993  Kayane et al. ............................. 424/42
5,520,926  5/1996  Ferguson .................................. 424/443

FOREIGN PATENT DOCUMENTS 2 265 310  9/1993  United Kingdom .
2 288 118  10/1995  United Kingdom .
WO 90/01938 A1  3/1990  WIPO .
WO 91/09604 A1  1/1991  WIPO .
WO 93/18777 A1  9/1993  WIPO .
WO 97/05883 A1  2/1997  WIPO .

OTHER PUBLICATIONS

H.U. Bergmeyer Editor, "Methods of Enzymatic Analysis", Verlag Chemie, Weinheim vol. II, 292, (1993).

I. Sato et al., "Depolymerization of Hyaluronic Acid by D–Fructose 6–Phosphate", Biosci. Biotech. Biochem., 57(12), 2005–2009 (1993).

A. Waheed et al., "Quarternary Structure of the $M_r$ 46000 Mannose 6–Phosphate Specific Receptor: Effect of Ligand,, pH, and Receptor Concentration on the Equilibrium between Dimeric and Tetrameric Receptor Forms", Biochemistry 29 No. 10, 2449–2455 (1990).

*Primary Examiner*—Carlos A. Azpuru
*Attorney, Agent, or Firm*—Nixon & Vanderhye

[57] ABSTRACT

Mannose-6-phosphate is formulated by pH adjustment as a suspension or solution at pH 6 to 8, preferably 6.5 to 7.5 and preferably at a concentration of 65 to 300 mM. Suspensions can be made in viscous hyaluronic acid gels. These compositions are useful in wound healing, particularly to prevent or mitigate scar formation.

14 Claims, 1 Drawing Sheet

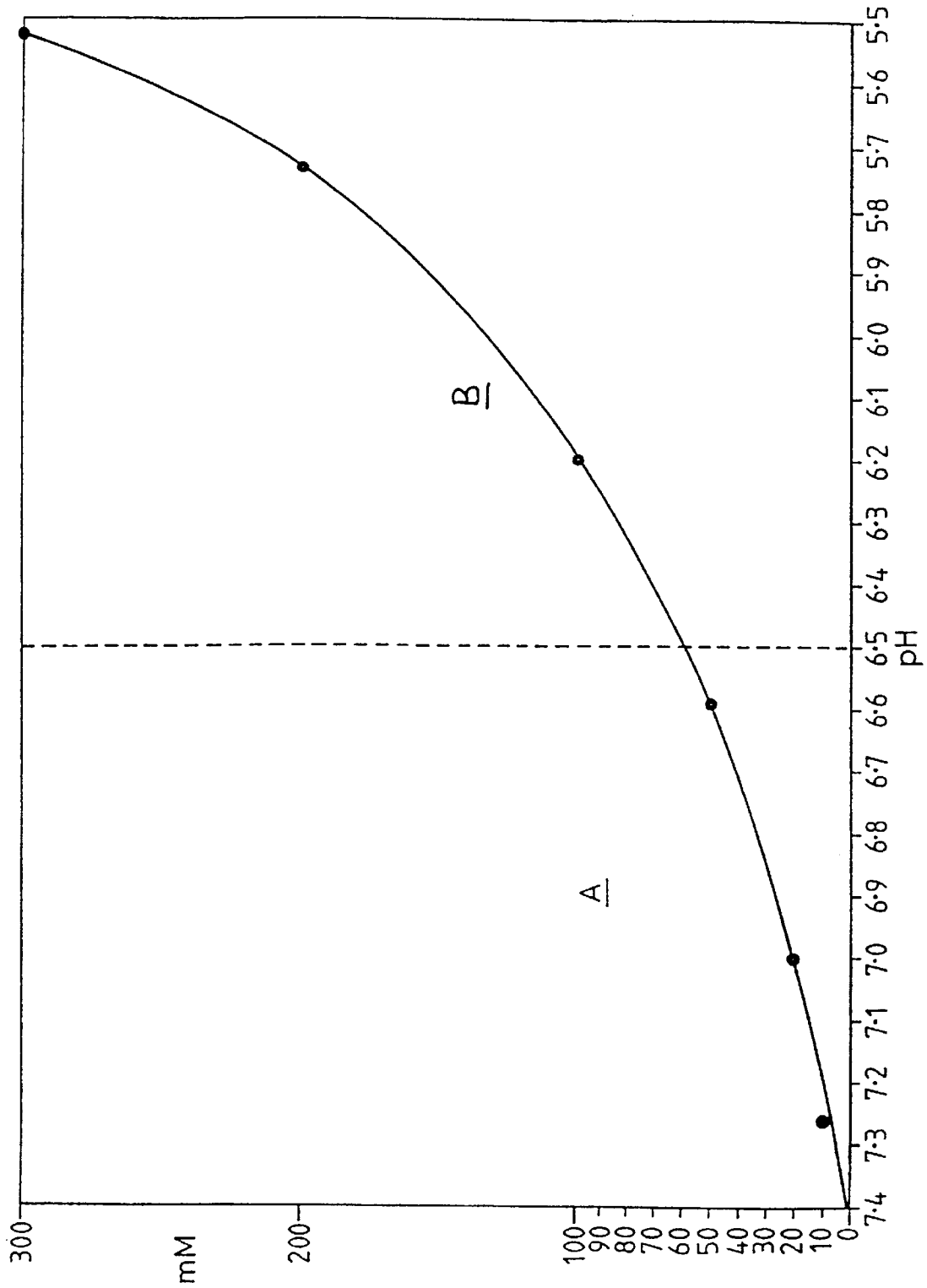

MANNOSE-6-PHOSPHATE COMPOSITION AND ITS USE IN TREATING FIBROTIC DISORDERS

This application is a 371 continuation of PCT/GB97/02076 filed Jul. 31, 1997 which is a continuation of United Kingdom Patent application No. 9616896.8 filed Aug. 12, 1996.

BACKGROUND OF THE INVENTION

1. Field of the Invention

This invention is in the field of prevention or mitigation of fibrotic disorder, especially scar formation in wound healing.

2. Description of the Related Art

It is a problem that, although wounds in humans and other mammals usually heal reasonably quickly, unsightly scar tissue is often formed. Scarring and other fibrotic disorders are an important clinical problem therefore, often resulting in adverse effects on function and growth as well as in some cases an undesirable cosmetic appearance.

Adult wound healing is characterised by acute inflammation, contraction and collagen deposition, responses likely to have been optimised for rapid wound closure and minimising infection. Scarring can be problematic in nearly all organs and tissues of the body, e.g. eyes, central nervous system, muscle, joints etc. Similar processes may also result in other fibrotic disorders which are common in many areas of medicine and surgery. For example, abdominal surgery often leads to intraperitoneal fibrous adhesions and/or strictures, whilst fibrotic retinopathy, scarring following glaucoma surgery, proliferative vitreoretinopathy, keloids, skin diseases e.g. epidermolysis bullosa, scieroderma, systemic sclerosis, pulmonary fibrosis, glomula nephritis, scarring of the central nervous system following, for example a stroke or neurosurgery and hepatic cirrhosis are significant medical problems. A major medical objective is therefore the reduction and ideally, the prevention of scarring and other fibrotic disorders.

WO93/18777 (British Technology Group Ltd) describes the use of mannose-6-phosphate for the treatment of fibrotic disorders. It accelerates wound healing and also prevents or mitigates scar formation. It is suggested in this patent application that the mannose-6-phosphate (M6P) may be formulated in any conventional way with a variety of carriers including for example hyaluronic acid. The suggested concentration of M6P is 10–60 mM. Best results were reported at 20 mM. while 100 mM gave a poor result, worse than the control. It is a problem to improve the results obtained in the WO 93/18777 patent application.

SUMMARY OF THE INVENTION

It has now been found that when the pH of solutions and suspensions of M6P is within the range 6.5 to 8, improved wound healing can be obtained at higher concentrations of M6P.

The present invention therefore provides a solution or suspension of a M6P-providing compound, which is M6P itself or a bioprecursor thereof or a polymer comprising at least one M6P residue, having a pH within the range 6.5 to 8. Usually the concentration is 50–400 mM, typically 65–300 mM preferably 65–120 and even more preferably 80–120 mM. Independently thereof, more preferably the pH is 6.5 to 7.5, most preferably 7 to 7.4.

To achieve the desired pH, addition of alkali, for example sodium hydroxide, will usually be necessary. Thus, for example, 100 mM M6P in physiological saline (pH 7.4) is too acidic and so requires the pH to be raised. Solutions of monosodium mannose-6-phosphate of low M6P molarity, say less than 60 mM, will normally have a pH of 6.5 to 7 without any pH adjustment. It is intended, however, to include those solutions within the scope of the invention by requiring that they be pH-adjusted with alkali to a higher pH within the range 6.5 to 8 than they would otherwise have. For removal of any perceived doubt, it is hereby confirmed that a solution or suspension of M6P, to which no pH adjustment has been made is expressly excluded from the scope of the present invention.

Also excluded from the compositions of the invention are compositions containing mannose-6-phosphate specific receptors. Mannose-6-phosphate specific receptors would bind the mannose-6-phosphate and so make less of it available. This disclaimer arises from the reference Waheed et al. Biochemistry 29, 2449–2455 (1990), which discloses the isolation of mannose-6-phosphate specific receptors in dimeric and tetrameric forms and experiments in which a receptor preparation is incubated at pH 7.5 with 5 mM mannose-6-phosphate, in order to explore whether oligomerisation of the receptor is influenced by ligand binding.

Invention resides in the compositions per se as well as for use in the prevention or mitigation of fibrotic disorders, especially for use in wound healing, in humans and in animals.

The invention includes the medical use of the above compositions, to the extent permitted by patent laws of the various countries of the world. Thus, in Europe it includes the use of the compositions in the manufacture of a medicament for the prevention or treatment of fibrotic disorders, especially for wound healing. In the U.S.A. and Australia it includes a method of prevention or treatment of fibrotic disorders in a human or animal, which comprises applying to the site of an expected or actual fibrotic disorder, especially a wound, an amount of a composition of the invention effective to prevent or treat said disorder and especially to inhibit scar formation in a wound.

The invention is particularly of interest for treating eye wounds and therefore provides a dispenser for application of an amount of gel or ointment suitable for the eye or of eyedrops, the dispenser containing a composition of the invention.

BRIEF DESCRIPTION OF THE DRAWING

The sole FIGURE is a plot of the molarity of monosodium mannose-6-phosphate in phosphate-buffered saline, which, before addition of the M6P is at pH 7.4, on the ordinate (y-axis) against pH on the abscissa (x-axis).

DESCRIPTION OF THE PREFERRED EMBODIMENTS

The M6P may be present in the form of the free phosphoric acid or a pharmaceutically acceptable mono- or di-salt thereof, for example a sodium, calcium, magnesium or barium salt. It may also be present in any polymeric form comprising at least one and preferably at least two M6P residues. In a di- or poly- saccharide M6P residue(s) may be 1,4- or 1.6- linked to neighbouring M6P or other saccharide residues. Polymers of up to 20 M6P monomers are envisaged, preferably up to 10 monomers. Other polymeric forms are possible including those wherein M6P residues are pendant from a backbone of a polymer and also polymers of M6P and HA. The M6P can also be in the form of a bioprecursor, i.e. a compound which is converted in situ (after application to the body) to the M6P. This can be achieved, for example, by linking a sugar alcohol group of the M6P to an appropriate acid to form an ester, in which this ester linkage is more readily hydrolysable than the phosphate linkage of M6P. Other forms of compound which will release M6P under hydrolytic, enzymatic or other conditions prevailing in the appropriate location in the body of the fibrotic condition to be treated, especially in wounds in the skin, will be evident to chemists and are encompassed in the definition of the M6P for the purposes of this invention. Hereinafter, the invention is described primarily by reference to M6P itself, for the sake of brevity. The same principles apply mutatis mutandis to the other M6P-providing compounds referred to above.

The M6P composition, whether as a solution or suspension, is pH-adjusted with any compatible alkali, especially sodium hydroxide, and formulated to give a concentration preferably from 20 mM upwards, especially from 50 mM upwards and most preferably 65–300 mM. The optimal concentration appears to be 80–120, especially about 100 mM. While the preferred form of M6P is a sodium salt, the concentrations are applicable to other forms of M6P. In the case of polymers, molarity should be with respect to M6P residues and in the case of bioprecursors based on the molarity of M6P equivalent, e.g. if 1 mole of precursor liberates 1 mole of M6P, the molarities of precursor are as above, but if 1 mole of precursor liberates 2 moles of M6P, the molarity of precursor is halved.

Without pH adjustment, many of these formulations would result in an undesirably acid pH. Even in phosphate-buffered saline (PBS), monosodium M6P at 65 mM gives a pH as low as 6.45. Higher M6P concentrations give an even lower pH. Thus, in the particular case illustrated in the drawing, using monosodium M6P dissolved in PBS, pH 7.4, the area B above the curve, to the right hand side of pH 6.5, represents concentrations of M6P (60 mM and above) which would give a pH below 6.5 without pH adjustment. The area A above the curve, at and to the left hand side of pH 6.5, represents concentrations of M6P (less than 60 mM) which would give a pH of above 6.5 without pH adjustment. Thus, a solution of monosodium M6P in PBS of 60 mM or above will require pH adjustment to raise the pH to 6.5 or above. While for lower concentrations of monosodium M6P in PBS a pH of 6.5 or above is obtained without pH adjustment, it is preferable to raise the pH in order to attain the more favoured range of 7.0 to 7.5 and therefore the invention makes it a requirement for the pH to be raised, regardless of the concentration of M6P. Since M6P is hydrolysed at alkaline pH, a pH of not higher than 7.5 is suggested, with an upper limit of about 8.

Formulation of M6P with hyaluronic acid (HA) is beneficial to wound healing. That is, the HA is acting not merely as an inactive carrier, but a co-ingredient which exerts a positive effect. Since HA used alone does not appear to promote wound healing, this is a surprising effect. Contrary to the finding of WO 93/18777, higher concentrations of M6P in HA, formulated as a viscous suspension, give an excellent effect in wound healing. Where the pH-adjusted M6P is formulated with hyaluronic acid (HA), a high loading of M6P can be achieved.

The HA may have any of a variety of average molecular weights ranging from 0.7 to 3 million, preferably 0.75 to 2.25 million and most preferably 1 to 1.75 million. It will be formulated to produce a suitable viscosity, so the higher the average molecular weight of the HA, in general, the lower the concentration thereof required. Lower m.w. HA is, however, easier to manufacture. Preferably HA of average m.w. $1.3 \times 10^6$ is used. The concentration of HA of average m.w. $1 \times 10^6$ to $1.5 \times 10^6$ is preferably in the range 0.5 to 2% by weight of the total composition. The gel viscosity is preferably in the range from 20,000 to 50,000 centipoise, especially 20,000 to 30,000.

M6P may be formulated in the compositions of the invention with any polymer which is (a) non-harmful to a wound ("biocompatible"), (b) non-inflammatory (does not cause inflammation at the wound site) and (c) can be absorbed into the site of the wound ("bio-absorbable" or "bio-resorbable"). It should be capable of releasing a concentration of M6P within the above-stated preferred ranges over at least 3 days and preferably over at least 7 days from application. Examples of suitable such polymers are polylactic acid, polyglycolic acid, polygalactide, polylactide and polymethylene carbonate. On the other hand, methyl cellulose and polyacrylic acid cause inflammation and so are unsuitable.

The compositions of the invention may be prepared in any possible form. For example, they may be adapted for topical administration as a gel, cream, lotion or ointment. These will be formulated in the conventional way and include aqueous or oleaginous vehicles or carriers and may further include antiseptics and other agents conventional in wound treatment. They may also be formulated as sterile injectable or syringeable solutions which can be formulated with any appropriate conventional solvent, e.g. in physiological saline (0.9% w/v NaCl). However, it will be appreciated that the specific form of the M6P and hyaluronic acid (HA) combination is as a viscous gel.

A particularly convenient way of applying the compositions of the invention will be by way of an impregnated or coated wound dressing, such as a bandage, plaster, absorbent pad or polymeric or hydrogel dressing, e.g. of collagen, sodium alginate or polyvinyl chloride. The dressing, will normally be stored under sterile conditions, ready for use. For internal treatments, an implant comprising a polymer, as carrier, and the composition of the invention is suggested.

Although the invention is primarily of interest in relation to skin wounds, whether arising through surgery or otherwise, including severe abrasions, lacerations and burns, it is also applicable to other kinds of lesion, e.g. photodamage of skin, keloids, hypertrophic scars, tendon damage, crush injury, proliferative vitreoretinopathy and scarring following glaucoma surgery, CNS injury resulting in scar tissue for example following stroke or neurosurgery, tissue adhesions, for example peritoneal adhesions or those produced following major abdominal or pelvic surgery, scarring in blistering skin diseases, e.g. epidermolysis bullosa, scleroderma, systemic sclerosis, liver and lung fibrosis and other disorders, for example those mentioned in connection with WO91/04748 (La Jolla).

A particularly important aspect of the invention lies in the treatment of tissue disorders leading to fibrotic disorders in relation to the eye, especially those leading to glaucoma relapse post surgery or epi-retinal membrane formation where a tear in the eye tissue leads to fibrosis with contraction and wrinkling of the retina or scarring of the cornea following injury. The invention includes particularly sterile eyedrop solutions of the M6P. They may be applied from a dispenser such as a squeezable plastic bottle having an eyedrop-providing nozzle or from a container fitted with a lid having a dropper attached to the lid extending internally of the container. Gels and ointments may be dispensed from tubes having nozzles of small diameter conventional in eye formulations.

Another important aspect of the invention lies in the treatment of skin wounds and fibrotic disorders occurring in relation to skin wounds e.g. keloids and hypertrophic scars. The formulation of the current invention promotes wound healing and reduces scar formation. The healing of tendons and ligaments is also improved by the invention.

The mode of application of the compositions of the invention will normally be topical, e.g. to a wound (inside and/or around it), but in appropriate cases subcutaneous or intradermal or intra-tissue e.g. tendon injection, or implantation may be required in order better to reach the affected tissue. In extreme cases intramuscular, intravenous or intraocular injection may be advisable. Preferably the M6P is applied to the affected area for at least the first three days of treatment, preferably at least twice per day.

The invention is illustrated by the following Examples. "Bioclusive" is a Registered Trade Mark. Throughout, M6P was used as the monosodium salt.

EXAMPLES

Effect of Mannose-6-Phosphate on Wound Healing in Rats

Method

Four linear full thickness incisions, 1 cm in length to the depth of the panniculus carnosus were made on the dorsal skin of male Sprague-Dawley rats, 250 g in weight. The incisions were made 1 cm from either side of the midline, 5 and 8 cm from the base of the skull. The midline is a line following the backbone from head to tail, longitudinal with respect to the animal. The wounds were thus longitudinal, parallel to the backbone. The wounds were left unsutured to heal by secondary intention. At least four animals were used in each treatment group at every time-point. Each animal always had its own control wound. A "treatment group" refers to the treatment which each animal within a group received. The position on the animal of each specifically treated wound was rotated between replicates to allow for any positional effects. Four animals per time-point were randomly assigned to each of two treatment groups, receiving 100 $\mu$l injections (50 $\mu$l to each side of the wound), before wounding (day 0), and on days 0–7 postwounding. Control wounds were injected with PBS alone. Wounds were harvested on day 80 postwounding. Wounds were harvested by excision from the surrounding tissue. Each wound was bisected, half the wound was rapidly frozen in a commercially available embedding medium "OCT" for cryosection and immunostaining and half fixed in formaldehyde for wax embedding and histology. Wax sections were routinely stained with haematoxylin and eosin, picrosirius red and Massons Lille trichrome, to display collagen fibre thickness, density and orientation to enable assessment of scar quality.

Histological sections (4–10 per wound) were taken and scored by trained and validated investigators according to a visual analogue scale. This is a 10 cm. line where one end (0) represents normal skin and the other end (10) the worst possible scar. A single score, being the mean of the scores given by two trained investigators, was then assigned to each wound and the mean of these scores for the number (n) of wounds was determined.

The Effect of pH on the Anti-Scarring Activity of M6P

The pH of M6P in solution in PBS was measured and it was found that an acid solution was formed. The pH was concentration-dependent, with the highest concentration solutions being the most acidic. At concentrations of 100 and 300 mM M6P the pH of the solutions was 6.2 and 5.5 respectively. Experiments were undertaken to determine whether the early inhibitory effects of M6P on wound healing observed were due to the low pH, rather than the osmolarity of the solution.

The influence of pH on the anti-scarring effect of M6P was investigated by administration to rats of a range of M6P concentrations at physiological pH. M6P was dissolved in half the appropriate volume of sterile double-distilled water and the pH adjusted to 7.4 by adding a very small amount, about 10 $\mu$l, of 10M NaOH. The very fine adjustment was made using 1M NaOH and checking the pH with a pH meter. The solution was then made up to the required volume with 2× sterile PBS. The pH was re-checked, to ensure that it remained at 7.4. The solution was then filter-sterilised before use. M6P was administered to the wounds by intradermal injection, as described above. All concentrations of M6P were applied daily, prior to wounding (day 0) and for 7 days postwounding. Four animals per time point were randomly assigned to 2 treatment groups and the four wounds were treated with injections of either PBS alone, 10 mM 20 mM and 300 mM M6P or PBS alone, 50 mM, 100 mM and 200 mM M6P. Wounds were harvested on days 1, 3, 7 and 80 postwounding.

High concentrations of M6P had no deleterious effects on wound healing and in general, the highest concentrations of M6P resulted in the most reduction in scarring. The anti-scarring activity of M6P was evident when a concentration of 20 mM M6P was applied, but increasing the concentration to 100 mM further improved the quality of the scar. At concentrations in excess of 100 mM, no consistent further reductions in scarring were observed, but no deleterious effects on the healing process were observed. This shows that the previously reported reduced effects of high concentrations of M6P are not due to osmolality but to use of a sub-optimal pH and that after pH adjustment in accordance with the present invention the optimum dose is now 100 mM.

Reductions in angiogenesis, wound fibronectin content and monocyte and macrophage infiltration at 7 days post-wounding were all observed wounds treated with M6P at pH 7.4. These effects were all dose-dependent, i.e. increasing with increasing dose and compatible with a reduction in TGF$\beta$ activity at the wound site. At three days postwounding, wound fibronectin content was highest in M6P-treated wounds, with PBS only-treated wounds containing little fibronectin at this time point. This effect is consistent with a faster rate of healing in the M6P treated wounds.

Further experiments were conducted in the same way at constant molarity (100 mM) but variable pH (5.5, 7.4, 9.5).

It has been demonstrated that M6P is an effective anti-scarring agent and that the pH of the solution is critical to the activity of the molecule in vivo. The most effective treatment appears to be one which delivers a significant dose of M6P, around 100 mM, over an extended time period (0–7 days) postwounding.

The main results of these Examples are tabulated below.

Mean Scores Using Visual Analogue Scale

Histology sections taken at 80 days post-wounding were scored by two trained observers for scar quality using a 10 cm visual analogue scale, with no reference points, where 0=normal skin, 10=worst scar.

| M6P, pH 7.4, injections | | |
|---|---|---|
| | Mean score ± SEM | Number of wounds scored |
| Control | 7.1 ± 0.6 | 8 |
| 10 mM | 5.4 ± 1.1 | 4 |
| 20 mM | 4.2 ± 1.3 | 4 |
| 50 mM | 2.9 ± 1.1 | 4 |
| 100 mM | 3.5 ± 1.1 | 4 |
| 200 mM | 6.2 ± 0.9 | 4 |
| 300 mM | 5.0 ± 1.8 | 4 |

| M6P, 100 mM, injections | | | |
|---|---|---|---|
| | | Mean score ± SEM | Number of wounds scored |
| Control | pH 5.5 | 6.4 ± 0.7 | 4 |
| M6P | pH 5.5 | 2.5 ± 0.6 | 4 |
| Control | pH 7.4 | 6.6 ± 0.7 | 4 |
| M6P | pH 7.4 | 2.9 ± 0.6 | 4 |
| Control | pH 9.5 | 5.5 ± 0.6 | 4 |
| M6P | pH 9.5 | 5.3 ± 1.0 | 4 |

Note:
These figures suggest that a pH as low as 5.5 gives as good results as pH 7.4, but, qualitatively, the pH 7.4 results were recognisably better.

What is claimed is:

1. A composition comprising a solution or suspension of a sodium salt of mannose-6-phosphate at a concentration of from 65 to 300 mM and pH-adjusted with alkali to pH 6.5 to 8, excluding a composition containing mannose-6-phosphate specific receptors.

2. A composition according to claim 1 wherein the pH is 6.5 to 7.5.

3. A composition according to claim 2 wherein the pH is 7 to 7.5.

4. A composition according to claim 1 wherein the concentration is from 80 to 120 mM.

5. A composition according to claim 1, which further comprises hyaluronic acid, in a concentration effective to jprovide a viscous gel suitable for retention in or around a wound.

6. A composition according to claim 1, in a sterile form.

7. A composition according to claim 1, for use in wound healing.

8. A composition according to claim 6 for use in healing a wound in the eye.

9. A wound dressing coated or impregnated with a composition claimed in claim 1.

10. A composition according to claim 1, formulated for administration to the eye, as a gel, ointment or eyedrops.

11. A method of prevention or treatment of a fibrotic disorder in a human or animal which comprises applying to the site of an expected or actual fibrotic disorder, an amount of the composition of claim 1 effective to prevent or treat said disorder.

12. A method according to claim 11 wherein the site of the disorder is a wound.

13. A method according to claim 11 wherein the wound is a skin wound.

14. A method according to claim 11 wherein the wound is in the eye.

* * * * *